United States Patent [19]

Lemrow

[11] Plant 4,025

[45] Mar. 22, 1977

[54] ROSE PLANT

[75] Inventor: Marilyn R. Lemrow, Farmingville, N.Y.

[73] Assignee: F. Harmon Saville, Rowley, Mass.

[21] Appl. No.: 679,146

[22] Filed: Apr. 22, 1976

[51] Int. Cl.[2] ..... A01H 5/00

[52] U.S. Cl. ..... Plt./9

[58] Field of Search ..... Plt./9

*Primary Examiner*—Robert E. Bagwill

*Attorney, Agent, or Firm*—Vincent G. Gioia

EXEMPLARY CLAIM

1. A new and distinct variety of rose plant of the miniature class, substantially as shown and described, characterized particularly by recurrent flowers of rose pink coloring aging to a lighter lavender pink coloring with cream colored center and reverse marking highlighting the open bloom; in large conically shaped clusters of about 7 to 12 blooms per cluster on a vigorous but compact growing plant with abundant foliage and few thorns.

1 Drawing Figure

The present invention relates to a new and distinct variety of rose plant of the miniature rose class, which was originated by my crossing as seed parent the rose variety known as "White Fairy" and an unknown seedling as pollen parent.

Among the novel characteristics possessed by this new variety which distinguish it from its parents and all other varieties of which I am aware are: (1) recurrent rose pink blooms borne in conically shaped clusters displaying a light lavender pink tonality from a distance, (2) long lasting blooms on the plant and after cutting, having petals that drop off cleanly on aging and (3) a vigorous plant which is very "winter hardy" and has abundant foliage and growth with very few thorns. Asexual reproduction by budding of the new variety as performed in Essex County, Mass., shows that the foregoing and other distinguishing characteristics come true to form and are established and transmitted through succeeding propagations.

The new and improved rose variety which I have developed is an unusually fine bright pink miniature exhibiting vigorous but compact growth advantageous in a miniature variety and abundance of flowers. The flowers are borne in multi-bloomed, conically shaped clusters often having 7 to 12 blooms providing a generally symmetrical and pleasingly shaped inflorescence. The blooms are also good size for a miniature, i.e., 23–29 mm and are generally cup-shaped. The well formed, old rose pink buds display some multi-color characteristics and the flowers have a slightly yellow cast at the inner base of the petals as the bloom opens. Individual flowers appear a dusty rose pink on opening and change to a lighter lavender pink coloring as the bloom ages. An especially desirable feature of this new variety is that it has relatively few thorns.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "45B" is plate 45B of the Royal Horticultural Society Color Chart.

Parentage: Seedling.

*Seed parent.*—"White Fairy."

*Pollen parent.*—"Unknown Seedling."

Class: Miniature.

The following observations are made of specimens grown in a greenhouse at Essex County, Mass. during the month of February.

FLOWER

Blooming Habit: Continuous.

Bud:

*Size.*—7 to 10 mm.

*Form.*—Ovoid to cupped.

*Color.*—When sepals first divide — 54B. When petals begin to unfurl — 66C. When half-blown: inside of petals — 66D; reverse side of petals — 54B.

*Sepals.*Elongated, pointed, long-extending beyond the bud, serrated.

*Peduncle.*Length — short. Strength — erect, well balanced. Color — 146B.

Bloom:

*Size.*—Average size when fully expanded — 23 to 29 mm.

*Borne.*—Conically shaped clusters, 7 to 12 blooms per cluster; symmetrically arranged and showing cycle of bloom.

*Form.*—Each flower opens cupped with slight ruffled effect in petals, each petal somewhat pointed.

*Petalage.*—Number of petals under normal conditions — 23 to 28 occasionally displaying a few petaloids.

*Color.*—(During first two days) Petal color is 54B, with slight cream markings on some petal reverse sides upon opening. Inner petal portions (points of attachment) are yellowish. Generally tonality from a distance — as petals open inflorescence takes on a light lavender pink cast about 66D.

*Color Change*—As bloom ages — from dusty rose pink to lighter lavender pink with cream colored center and reverse markings highlighting the open bloom. General tonality — 66C changing to 66D as petals drop.

Petals:

*Texture.*—Medium for a miniature.

*Appearance.*—Smooth with good substance at outer margin of petals.
*Form.*—Slightly pointed.
*Arrangement.*—Regularly arranged, tendency to reflex on outer petals of older blooms.
*Petaloids in center.*—Few.
*Persistence.*—Drop off cleanly
*Fragrance.*—Slight.
*Lasting Quality.*—Very good on plant and as cut flower.

REPRODUCTIVE ORGANS

Stamens, filaments and anthers:
*Arrangement.*—Regularly arranged around styles.
*Color.*—154C.
Pollen: Color — 12B.
Styles: Thin, normal.
Stigmas: Color — 154C.
Hips:
*Shape.*—Globular.
*Size.*—About 6mm.
*Color.*—Orange-red 42B to 43B when mature.
*Do seeds protrude.*—No.

PLANT

Form: Vigorous, upright and spreading.
Growth: Very vigorous, good inner branching on main stems. Height attained — 15 to 18 inches.
Foliage: 5 to 7 leaflets.
*Size.*—Medium.
*Quantity.*—Abundant.
*Color.*—New foliage: upper side — near to and in between 146A and B; under side — near to and in between 146B and C. Old foliage: upper side — near to and in between 146B and C; under side — near to and in between 146B and C.
*Shape.*—Oval, pointed.

*Texture.*—Upper side — medium. Under side — medium.
*Edge.*—Serrated.
*Serration.*—Regular more pronounced toward tip; uniform on small leaves as well.
*Leaf stem.*—Color — same as old foliage. Under side — same as old foliage.
*Stipules.*—Medium length.
*Resistance to Disease.*—Blackspot — good. Mildew — good.
Wood:
*New wood.*—Color — 146D. Bark — smooth.
*Old wood.*—Color 146B. Bark — smooth.
Thorns:
*Thorns.*—Quantity: on main stalks from base — very few thorns; on laterals from stalk — almost none. Form — flat base with slight downward curve. Length — small, pointed. Color (when young) — near to 161B. Position — very few, irregular.
*Prickles.*—Quanity: on main stalks — none on main canes, few on underside of leaf stem; on laterals — none.
Winter Hardiness: Good winter hardiness.

I claim:

1. A new and distinct variety of rose plant of the miniature class, substantially as shown and described, characterized particularly by recurrent flowers of rose pink coloring aging to a lighter lavender pink coloring with cream colored center and reverse marking highlighting the open bloom; in large conically shaped clusters of about 7 to 12 blooms per cluster on a vigorous but compact growing plant with abundant foliage and few thorns.

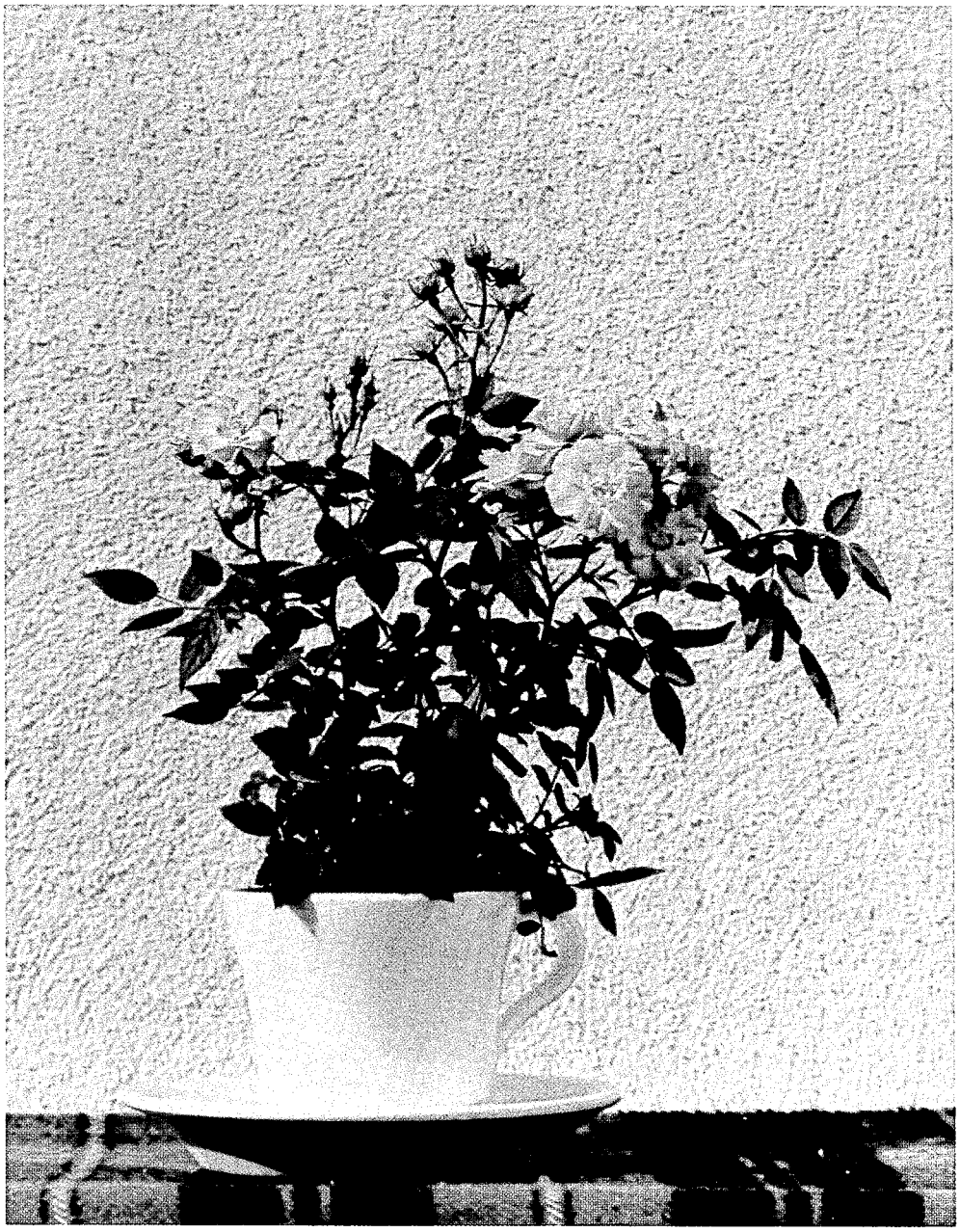

* * * * *